US 9,585,792 B2

(12) United States Patent
Fairclough et al.

(10) Patent No.: US 9,585,792 B2
(45) Date of Patent: Mar. 7, 2017

(54) SOUND MUFFLING HEADWEAR (71) Applicants: Jacob Frederick Fairclough, Salt Lake City, UT (US); Michele Renee Haley, Salt Lake City, UT (US)

(72) Inventors: Jacob Frederick Fairclough, Salt Lake City, UT (US); Michele Renee Haley, Salt Lake City, UT (US)

(*) Notice: Subject to any disclaimer, the term of this patent is extended or adjusted under 35 U.S.C. 154(b) by 1061 days.

(21) Appl. No.: 13/725,226

(22) Filed: Dec. 21, 2012

(65) Prior Publication Data

US 2013/0133671 A1 May 30, 2013
US 2016/0354252 A9 Dec. 8, 2016

Related U.S. Application Data (63) Continuation-in-part of application No. 12/351,352, filed on Jan. 9, 2009, now abandoned.

(60) Provisional application No. 61/020,641, filed on Jan. 11, 2008.

(51) Int. Cl.
*A61F 11/14* (2006.01)
*A42B 1/06* (2006.01)

(52) U.S. Cl.
CPC .............. *A61F 11/14* (2013.01); *A42B 1/068* (2013.01)

(58) Field of Classification Search
CPC A61F 11/14; A61F 11/06; A61F 11/02; A61F 11/12; A61F 11/00; A42B 1/068; A42B 1/06; A42B 3/16; A42B 3/163; A42B 3/166; A63B 71/10
USPC ..................................................... 2/209, 428
See application file for complete search history.

(56) References Cited

U.S. PATENT DOCUMENTS

| | | | | |
|---|---|---|---|---|
| 428,511 A * | 5/1890 | Moore | ..................... | A61F 11/14 2/209 |
| 2,325,150 A * | 7/1943 | Sahlmann | ............... | A61F 11/06 2/209 |
| 2,367,459 A * | 1/1945 | Corley | ................... | A42B 1/068 2/172 |
| 2,378,398 A * | 6/1945 | Fiedler | .................... | A61F 11/06 2/209 |
| 2,391,335 A * | 12/1945 | O'Brien | ................... | A42B 3/00 2/425 |
| 2,476,589 A * | 7/1949 | Driskill | .................... | A61F 11/14 128/866 |
| 2,597,508 A * | 5/1952 | Majewski | ............... | A61F 11/06 2/209 |
| 2,648,843 A * | 8/1953 | Hirschmann | ........... | A61F 9/026 2/431 |

(Continued)

FOREIGN PATENT DOCUMENTS

GB        EP 0085533 A2 *  8/1983    .............. A61F 11/14

*Primary Examiner* — Alissa L Hoey
(74) *Attorney, Agent, or Firm* — Pate Baird, PLLC (57) ABSTRACT

A headband, cap, hat, or the like worn by a child, particularly an infant, includes an embedded sound-attenuation system to protect hearing against loud sounds that might startle, awaken, or injure a wearer. Shells formed of a comparatively soft and flexible elastomeric material are secured against the head of a user, each enclosing an ear in an air tight chamber, to close down the transmission paths available to sound waves. The shells are impervious to air, and flexible to conform to the head when secured by the headgear in which the shells are embedded. Each shell is provided with a rim, sufficiently flexible to deform and deflect into complete, sealed contact with the head.

8 Claims, 8 Drawing Sheets

(56) References Cited

U.S. PATENT DOCUMENTS

| | | | |
|---|---|---|---|
| 2,738,514 A * | 3/1956 | Gondell | A42B 1/12 2/174 |
| 2,802,214 A * | 8/1957 | Hanks | A42B 3/166 128/866 |
| 3,311,921 A * | 4/1967 | Helm | A63B 71/10 2/209 |
| 3,506,980 A * | 4/1970 | Aileo | A61F 11/14 2/209 |
| 3,506,981 A | 4/1970 | Stewart et al. | |
| 3,525,103 A * | 8/1970 | Yonan | A61F 11/06 2/174 |
| 3,571,813 A | 3/1971 | Allen | |
| 3,588,914 A * | 6/1971 | Ihnat, Jr. | A42B 1/12 2/205 |
| 3,594,815 A * | 7/1971 | Reese | A42B 1/068 2/421 |
| 3,628,191 A * | 12/1971 | Douglas | A63B 71/10 2/421 |
| 3,686,691 A | 8/1972 | Anderson | |
| 3,780,379 A | 12/1973 | Kampman | |
| 3,795,014 A | 3/1974 | Simpson et al. | |
| 3,875,592 A * | 4/1975 | Aileo | A61F 11/14 2/209 |
| 3,944,018 A * | 3/1976 | Satory | A61F 11/14 128/866 |
| 3,952,158 A | 4/1976 | Kyle et al. | |
| 4,023,642 A * | 5/1977 | Korn | A61F 11/08 128/866 |
| 4,037,273 A * | 7/1977 | Labaire | A61F 11/14 2/209 |
| 4,064,362 A | 12/1977 | Williams | |
| 4,459,707 A | 7/1984 | Stallings | |
| 4,471,496 A * | 9/1984 | Gardner, Jr. | A61F 11/14 2/209 |
| 4,546,215 A * | 10/1985 | Ferraro | H04R 1/1058 2/209 |
| 4,616,643 A * | 10/1986 | Jung | A61F 11/06 128/866 |
| 4,654,898 A | 4/1987 | Ishikawa | |
| 4,796,307 A | 1/1989 | Vantine | |
| 4,802,245 A * | 2/1989 | Miano | A61F 11/06 2/209 |
| 4,830,138 A * | 5/1989 | Palmaer | A61F 11/14 181/129 |
| 4,872,219 A * | 10/1989 | Duncan | A61F 11/06 128/866 |
| 4,944,361 A | 7/1990 | Lindgren et al. | |
| 5,038,412 A | 8/1991 | Cionni | |
| 5,044,014 A | 9/1991 | Cornale et al. | |
| 5,046,193 A * | 9/1991 | Foresman | A42B 1/12 2/195.7 |
| 5,068,923 A | 12/1991 | Sjoqvist | |
| 5,080,110 A | 1/1992 | Weldon et al. | |
| 5,138,722 A | 8/1992 | Urella et al. | |
| 5,231,704 A | 8/1993 | Hildenbrand | |
| 5,243,709 A * | 9/1993 | Sheehan | A61F 11/14 2/209 |
| 5,285,530 A | 2/1994 | Nardone, Jr. | |
| 5,339,467 A * | 8/1994 | Brinkley | A61F 11/06 2/209 |
| 5,509,146 A | 4/1996 | Bryerton, Sr. | |
| 5,528,774 A | 6/1996 | Sanders | |
| 5,551,089 A | 9/1996 | Whidden | |
| 5,551,090 A | 9/1996 | Thompson | |
| 5,615,417 A | 4/1997 | Jackson | |
| 5,615,419 A | 4/1997 | Williams | |
| 5,718,001 A | 2/1998 | Wright | |
| 5,778,455 A * | 7/1998 | Joseph | A45D 44/12 2/174 |
| 5,887,286 A | 3/1999 | Waldron | |
| 5,920,912 A | 7/1999 | Patchett | |
| 5,996,123 A * | 12/1999 | Leight | A61F 11/14 128/867 |
| 6,298,493 B1 * | 10/2001 | Ambroise | A45D 44/12 128/866 |
| 6,353,938 B1 | 3/2002 | Young | |
| 6,484,324 B2 * | 11/2002 | Garofalo | B63C 11/12 2/428 |
| 6,499,146 B2 | 12/2002 | Bavetta et al. | |
| 6,557,179 B1 * | 5/2003 | Reuven | A42B 1/008 2/171.2 |
| 6,611,963 B2 | 9/2003 | Woo et al. | |
| 6,625,819 B1 * | 9/2003 | Tsai | A61F 11/14 181/129 |
| 6,678,897 B2 | 1/2004 | Lindgren | |
| 6,698,028 B2 | 3/2004 | Daw | |
| 6,880,174 B2 | 4/2005 | Prokop | |
| 7,024,013 B1 * | 4/2006 | Van Dam | A61F 11/14 2/209 |
| 7,028,343 B1 | 4/2006 | Watson | |
| 7,171,698 B2 | 2/2007 | Saffran | |
| 7,181,778 B1 * | 2/2007 | Garraffa | A61F 9/025 2/426 |
| 8,534,290 B2 * | 9/2013 | Karrman | A61F 11/14 128/867 |
| 2004/0172738 A1 | 9/2004 | Caine et al. | |
| 2005/0015851 A1 * | 1/2005 | Kaufman | A61F 9/04 2/208 |
| 2005/0028250 A1 | 2/2005 | Zaic | |
| 2006/0117469 A1 * | 6/2006 | Garofalo | B63C 11/12 2/428 |
| 2007/0044205 A1 | 3/2007 | Sato et al. | |
| 2007/0143907 A1 | 6/2007 | Hansson et al. | |
| 2008/0128198 A1 * | 6/2008 | Du | A61F 11/14 181/129 |
| 2008/0263749 A1 * | 10/2008 | Leong | A61F 11/14 2/209 |
| 2009/0205900 A1 * | 8/2009 | Purcell | A61F 11/14 181/129 |
| 2010/0054491 A1 * | 3/2010 | Griffin | A61F 11/14 381/71.6 |
| 2012/0124719 A1 * | 5/2012 | Michlitsch | A61F 11/14 2/423 |

* cited by examiner

SOUND MUFFLING HEADWEAR

RELATED APPLICATIONS

This application is a continuation of U.S. patent application Ser. No. 12/351,352 filed Jan. 9, 2009, which claims the benefit of U.S. Provisional Patent Application Ser. No. 61/020,641 filed on Jan. 11, 2008.

BACKGROUND

1. The Field of the Invention

This invention relates to head gear and, more particularly, to novel systems and methods for earmuffs.

2. Background of the Prior Art

Adults who are exposed to dangerous levels of noise may wear hearing protection. Shooters, factory workers who operate noisy machinery, industrial workers who work in noisy environments, and so forth may wear hearing protection. The two most common types of protection are the moldable, memory-foam, plugs that can be molded to a comparatively small diameter for insertion into the outer ear canal, and which then over a matter of seconds or minutes will expand to a larger diameter in order to occlude sound waves entering the outer ear canal of a wearer.

Shooters earmuffs' resemble private stereo headphones, being manufactured with a large, hard, plastic or other composite material cavity that surrounds the ear. The two, hemispherical, hard shells corresponding to the two ears of a user are often made of a plastic such a styrene or a styrene mixture, other structural materials, fiber-reinforced plastic, or the like. Each hemispherical shell is sufficiently large to fit around the respective ear of a user, receive the ear therein. Typically, a resilient liner is secured along the circumference of each shell in order to deform and deflect at the surface of the head of a user, in order to fit against the head of a user surrounding the ear.

Necessarily, such systems require substantial force to be applied to the shells by a spring formed in an arc passing from one shell up over the crown of the head and down to the other shell. The force is sufficient that some alignment is often required, giving rise to a pivot system by which each shell may pivot in at least one dimension, about at least one axis with respect to the powerful spring.

Infants are less likely to be in environments requiring hearing protection. Nevertheless, to avoid startling an infant, waking an infant, protect infant ears, or otherwise to provide attenuations of sound, conventional sound-attenuating earmuffs simply do not serve. Notwithstanding the inappropriate size, such a technique of using a spring force, typically applied by a steel spring, to apply a pressure force against the head of a wearer would be not only uncomfortable but dangerous to an infant. An infant can neither complain, identify the source of discomfort, nor participate in adjusting or finding another solution to the problem.

Nevertheless, parents often desire to reduce noise to which children are exposed, particularly during sleep, when walking in a stroller along streets bearing substantial traffic, and so forth. What is needed is a sound-attenuation system more in keeping with the physical realities of infant physiology, sound deadening technology, ease of use, comfort, and so forth.

BRIEF SUMMARY OF THE INVENTION

In accordance with the problems and adult solutions discussed hereinabove, in one embodiment, the apparatus and method in accordance with the invention may rely on embedding various mechanisms for attenuating, deadening, and otherwise muffling sound impinging on the ears of an infant into other infant headgear. This application also incorporates by reference U.S. patent application Ser. No. 12/351,352, filed on Jan. 9, 2009.

A user of adult headgear virtually never uses sound-deadening equipment with a winter cap. These two items are mutually exclusive in that each needs to occupy the same space near the head of a user. In contrast, an infant may be provided with a cap, hat, blanket, other clothing, and so forth to protect against comparatively cooler weather.

In one embodiment of an apparatus and method in accordance with the invention, sound-deadening devices are embedded in headwear or headgear such as headbands, caps, hats, and so forth. In one currently contemplated embodiment, the ears of a wearer (infant) are each enclosed in a respective flexible shell.

These contrast to adult systems, which require substantial structural strength and stiffness the shells. Such stiffness is required in order to connect to and support the loads imposed by the steel springs clamping the shells together toward one another on the head of a user. Shells in accordance with present invention may be formed of a compliant elastomeric material, such as silicone, urethane, or other non-structural material. The softness, stiffness, durometer-measured hardness, and bending deflection of the shells approximate those of the shells.

The shells surrounding the ears of the user in accordance with the current invention provide deadening of sound directly through the walls of the shells, unlike adult systems, which simply transmit the sound therethrough to be deadened elsewhere. Likewise, in an apparatus and method in accordance with the invention, the shell may be sealed against the side of the head of a user by a combination of distortion of a liner portion of the shell, and deflection of the shell, changing its fundamental shape to conform by bending about the cranium of a wearer.

Additional mechanisms, including elastomeric, dampening materials, comforting or warming fabrics, and the like may be installed in the interior of the shells in order to add comfort, support, or sound dampening for the benefit of a wearer.

Avoiding the forces along an axial direction with respect to the ear canal of a user, the shell may be supported by ties, ligatures, laces, straps, or the like. Typically, a flap portion of headgear, may hold some or all of the shell, and have a tie placed at one extremum, opposite the hat. Accordingly, rather than applying axial force along the shell, in the direction of the gear of a wearer, an apparatus and method in accordance with the invention may rely on circumferential loading along an arc proceeding from proximate the hat down through the ear flap, and under the chin of a wearer. Forces will necessarily be less applying pressure to the head of a wearer from the shells. By the same token, inasmuch as the shells are themselves quite flexible, fabricated from elastomeric materials in comparatively thin gauges, a user will not have to serve as a resistance to a strong spring. Instead, the shells are readily deformable about any radius or diameter in response to the draw of a line such as a tie, lanyard, strap, or the like. Accordingly, complete contact can be assured.

Moreover, in an apparatus and method in accordance with the invention, a wearer need not be troubled by sound leakage such as would occur in conventional headgear. Rather, in one embodiment, the elastomeric material of the shell is sufficiently impervious to fluid transport as to block frequencies of sound in substantially all ranges. Put another way, the elastomeric material of the shell enables blocking, by the shell, sound propagated from the environment surrounding the wearer against impingement upon the eardrum of a user. Necessarily, some limits exist to the ability to attenuate sound. Nevertheless, as a general proposition, sound waves, as other waves pass through openings characterized according to their relationship to the wave length passing therethrough. Sound waves tends to be attenuated best when subjected to passage through an opening much less than the characteristic length of the waves. Here, the polymeric or elastomeric polymer of which the shells are formed may be continuous and contiguous throughout the shell, thus attenuating all wavelengths. In one embodiment, the shell comprises an outer wall, an offset wall, a rim, and a flange, all formed continuously, contiguously and homogeneously of a single material.

Of course, the amount of energy in a sound wave also affects the ability to attenuate the sound. Thus, it may quite impossible to eliminate all sound, notwithstanding all sound wave frequencies may be attenuated to some extent.

BRIEF DESCRIPTION OF THE DRAWINGS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

DETAILED DESCRIPTION OF THE PREFERRED EMBODIMENTS

Sound muffling headwear is provided herein that includes a flexible circumferential band. As used herein, the term circumferential band shall be broadly understood to mean a band that forms a continuous perimeter, although it may be formed of more than one piece. In at least one example, the sound muffling headwear includes flexible housings coupled to or integrated with the circumferential band. The flexible housings are configured to receive earmuffs. When assembled, the circumferential band and the flexible housing cooperate to place the earmuffs in proximity with a wearer's ears to thereby provide muffle or reduce ambient noises detected by the wearer, such as a child.

In at least one example, the circumferential band can be made of a fabric material with a soft hand, such as a fleece material. Such a configuration can allow a wearer, such as a child, to comfortably wear the headwear in a variety of settings. Allowing the user to comfortably wear the headwear can in turn help ensure that the user will not become annoyed by the headwear and remove it. As a result, such a configuration can help ensure that the headwear will remain in place and thus be allowed to muffle sound to thereby protect the wearer. The circumferential nature of the flexible band can also further ensure that the headwear will remain in place.

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry.

Figure 1:
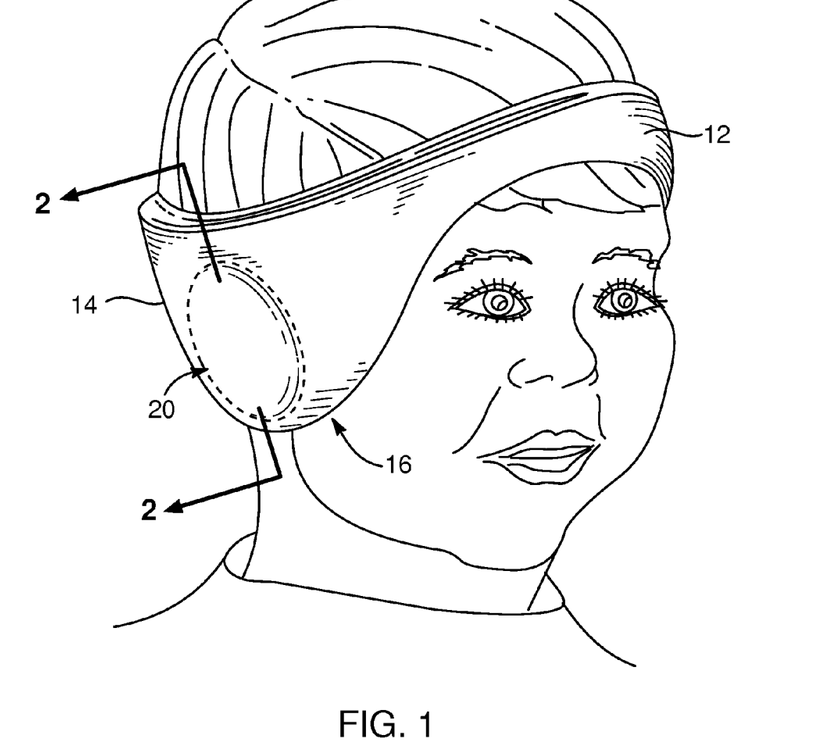
FIG. 1 is a perspective view of one embodiment of an apparatus in accordance with the invention worn by a user.

FIG. 1 illustrates a perspective view of sound muffling headwear 10. As illustrated in FIG. 1, the sound muffling headwear 10 includes a flexible circumferential band 12. The sound muffling headwear 10 further includes housings 14 coupled to or integrated with the flexible circumferential band 12. The housings 14 are configured to receive earmuffs 20. The earmuffs 20 can be secured to the housings 14 in any suitable manner. In at least one example, the earmuffs 20 can be sewn into the housing 14. In other examples, the housings 14 can be configured as flapped pockets such that the earmuffs 20 can be removably coupled to the housings 14. It will be appreciated that the earmuffs 20 can be secured to the housings 14 in any suitable manner.

The flexible circumferential headband 12 can be formed of any suitable material, including cloth or fabric materials. In at least one example, the flexible circumferential band 12 can be formed of a fleece material. The flexible circumferential band 12 can also include elastic properties which allow the flexible circumferential band 12 to stretch to be readily fitted to a wearer. In at least one example, the circumferential band 12 can have an adjustable circumference. One such example can be provided to include headwear configured as an adjustable cap, such as an adjustable baseball-style cap.

Similarly, the housings 14 can be formed of flexible material, such as a cloth or fabric material. The housings 14 can be formed of the same or different materials than the flexible circumferential band 12. In at least one example, the housings 14 can be formed of a cloth material with a soft hand and wicking properties to allow the earmuffs 20 to be comfortably maintained in close proximity to a wearer's ears.

Figure 2:
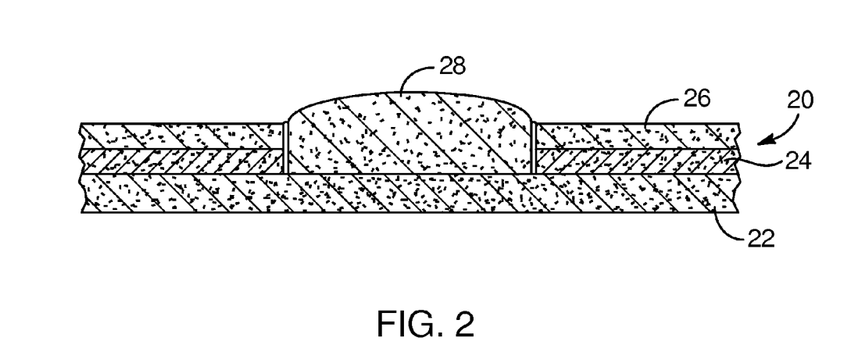
FIG. 2 is a cross-sectional view of one embodiment of a sound-attenuation insert in one embodiment of an apparatus in accordance with invention.

FIG. 2 is a cross-sectional view of one of the earmuffs taken along section 2-2 of FIG. 1. As illustrated in FIG. 2, the earmuff 20 can include a base layer 22 and additional layers 24, 26. The base layer 22 can be formed of any flexible material with sound muffling properties. In at least one example, the base layer 22 can be formed of a neoprene material. In other examples, the base layer 22 and/or the other layers 24, 26 can be formed of closed cell rubber, closed cell foam, memory foam, or any other material.

The additional layers 24, 26 can be secured to each other and to the base layer 22 to form a recess. In at least one example, layer 24 can be formed of a sound muffling material, such as neoprene. Layer 26 can also be formed of a softer material having sound muffling properties. Further layer 26 can be formed of a material that conforms to the wearer. In at least one example, layer 26 can be formed of a memory foam material. The layers 24, 26 cooperate to form a recess configured to engage or receive a wearer's ear.

In at least one example, the recess can be at least partially filled with a soft material 28 that can have sound muffling properties as well. For example, the recess can be at least partially filled with a soft foam material that can have antibacterial properties.

The layers 24, 26 can be secured to the base layer 22 in any suitable manner. In at least one example, silicone, such as aquarium-grade silicone gel, can be used to secure layer 24 to the base 22 and/or to secure layer 26 to layer 24. It has been found that the use of silicone provides additional sound muffling properties, thereby enhancing the efficacy of the noise muffling headwear in isolating noise.

In the illustrated example, the earmuffs 20 are part of noise muffling headwear that is configured as a headband. It will be appreciated that other configurations are possible. Several additional configurations will be described in more detail below.

Figure 3:
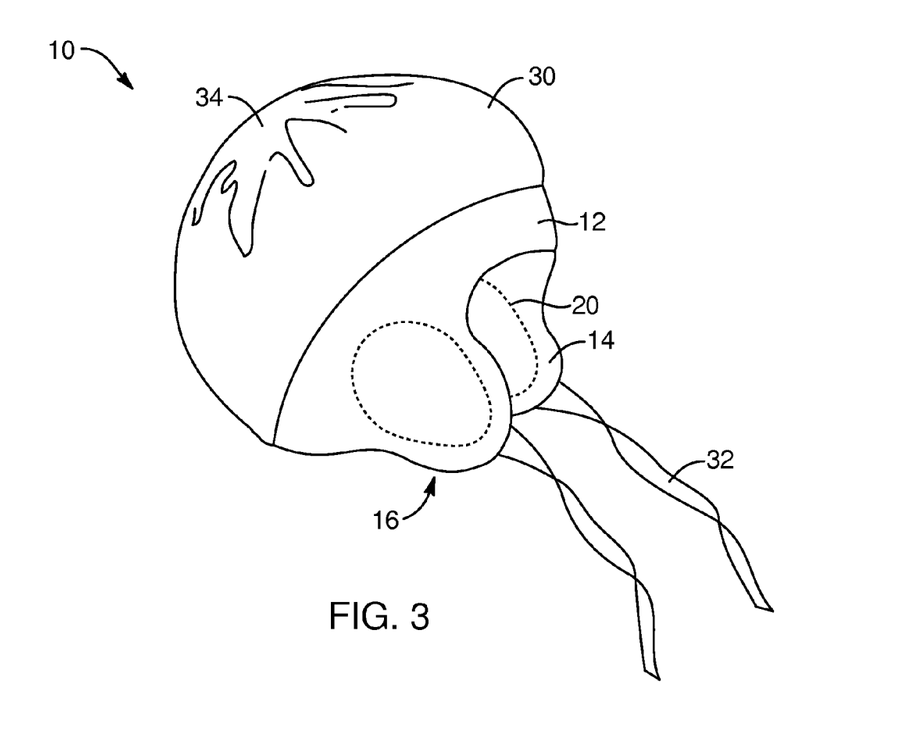
FIG. 3 is a perspective view of one embodiment of headgear suitable for including a sound-reducing earmuff in accordance with the invention.

FIG. 3 illustrates noise muffling headwear 10 according to one example. As illustrated in FIG. 3, the noise muffling headwear 10 includes an optional top portion 30 secured to or integrated with the flexible circumferential headband 12 and optional lower straps 32 integrated with the housings 14. Accordingly, the noise muffling headwear 10 can be configured as a beanie or a touque.

Figure 4:
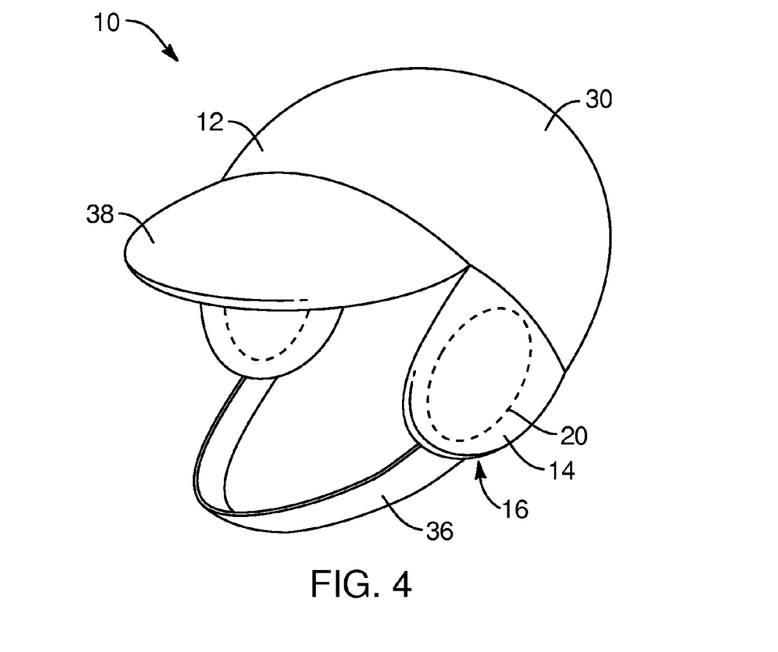
FIG. 4 is alternative embodiment of headgear for containing sound-reducing earmuffs.
Figure 5:
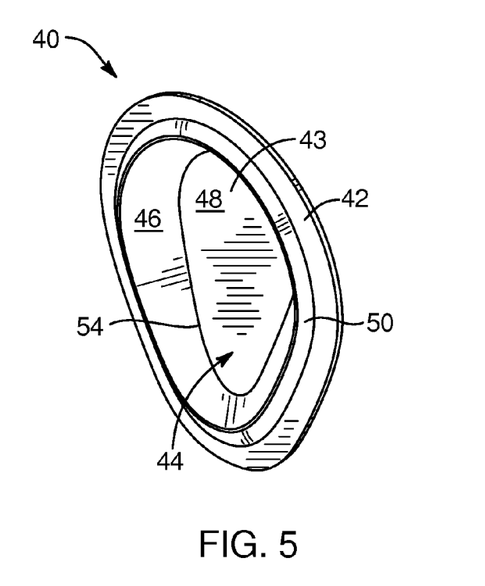
FIG. 5 is a left side perspective view of one embodiment of a shell for an earmuff for reducing sound, in accordance with the invention.
Figure 6:
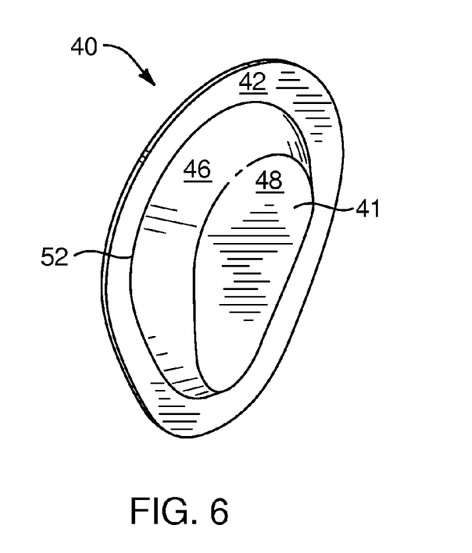
FIG. 6 is a right side perspective view thereof.
Figure 7:
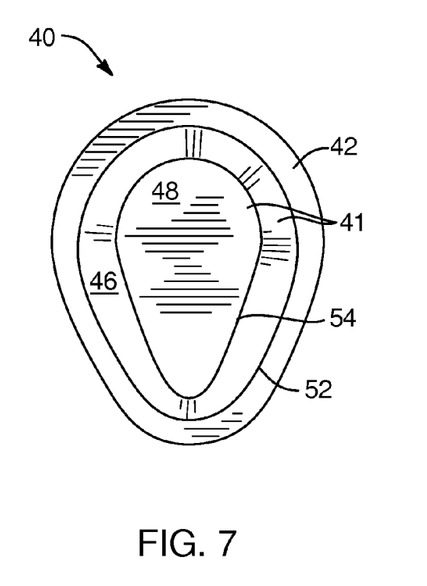
FIG. 7 is a right side elevation view thereof.
Figure 8:
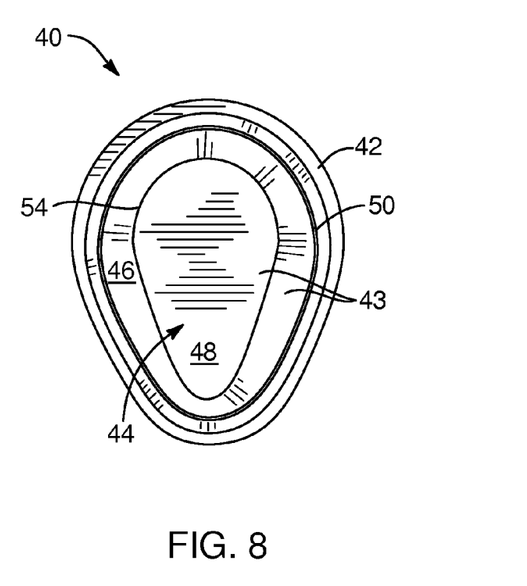
FIG. 8 is a left side elevation view thereof.
Figure 9:
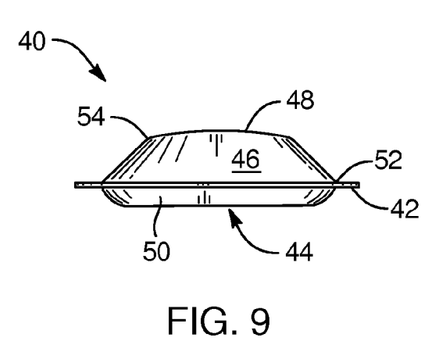
FIG. 9 is a top plan view thereof.
Figure 10:
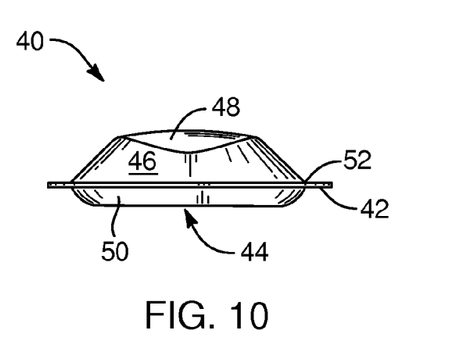
FIG. 10 is a bottom plan view thereof.
Figure 11:
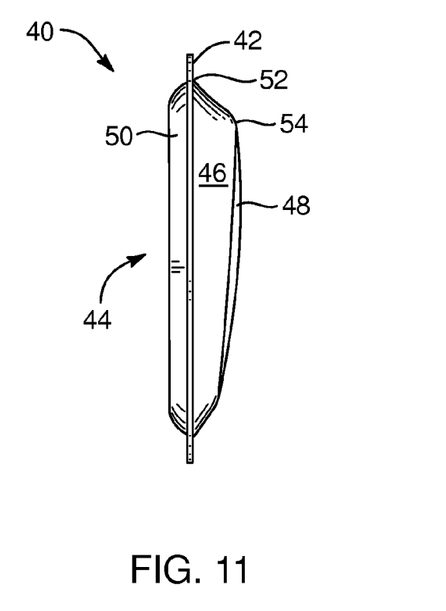
FIG. 11 is a rear elevation view thereof.
Figure 12:
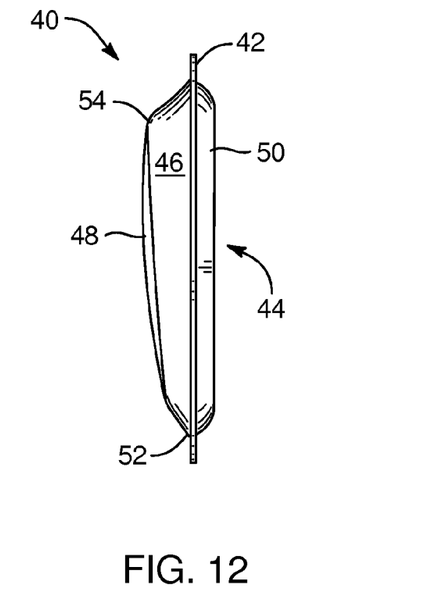
FIG. 12 is a front elevation view thereof.
Figure 13:
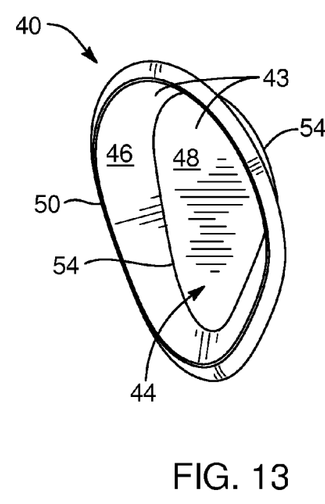
FIG. 13 is a left side perspective view of an alternative embodiment of a shell in accordance with the invention.
Figure 14:
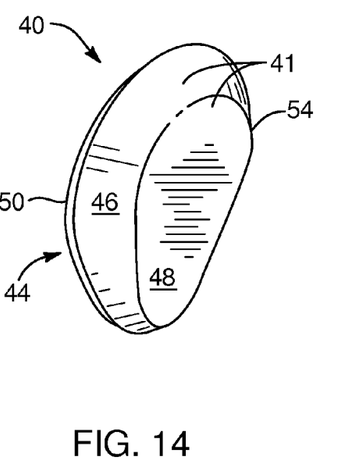
FIG. 14 is a right side perspective view thereof.
Figure 15:
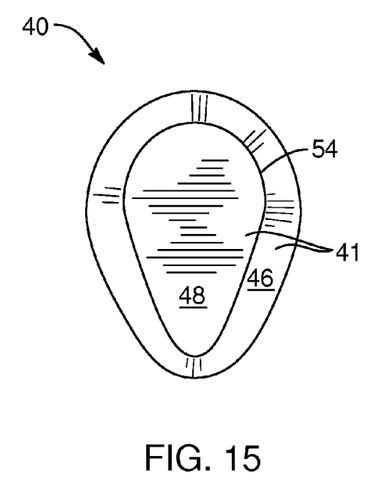
FIG. 15 is a right side elevation view thereof.
Figure 16:
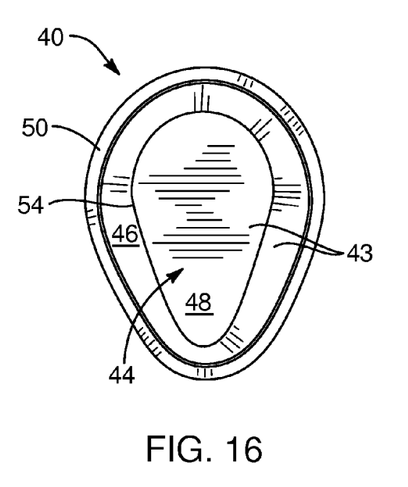
FIG. 16 is a left side elevation view thereof.
Figure 17:
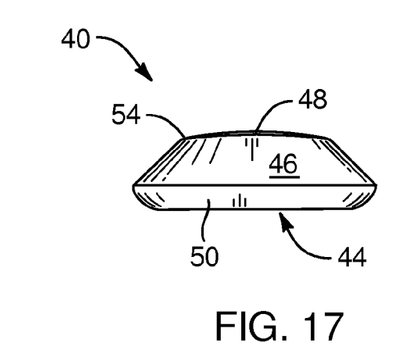
FIG. 17 is a top plan view thereof.
Figure 18:
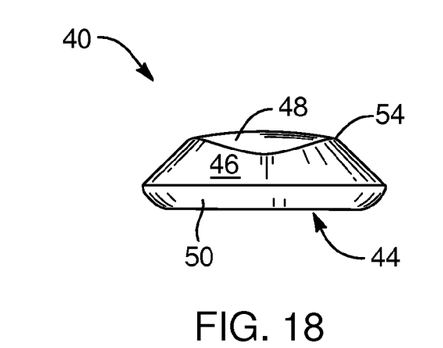
FIG. 18 is a bottom plan view thereof.
Figure 19:
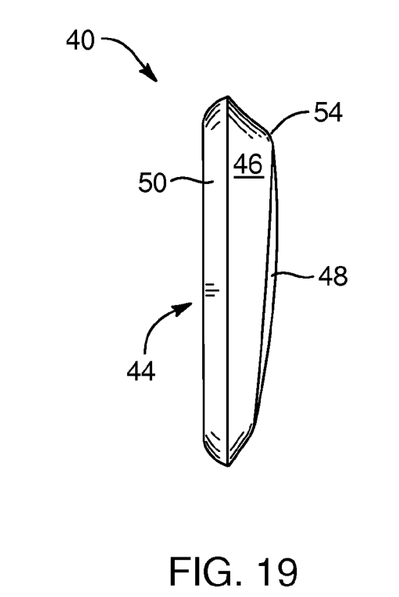
FIG. 19 is a rear elevation view thereof.
Figure 20:
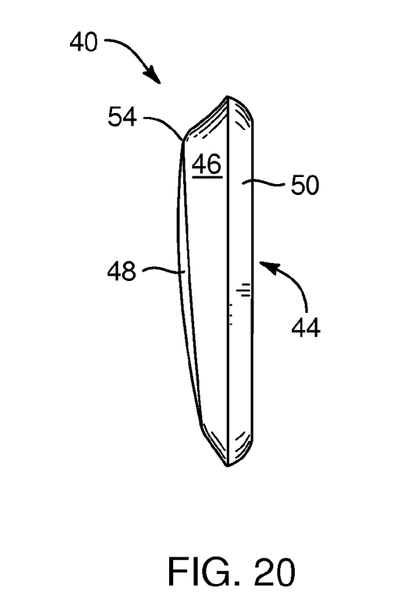
FIG. 20 is a front elevation view thereof.

In other examples, such as illustrated in FIG. 4, noise muffling headwear 10 can also include a bill 38 coupled to or integrated with the flexible circumferential headband 12 such that the noise muffling headwear 10 is configured as a cap. Accordingly, the noise muffling headwear can be configured in any number of ways.

With respect to the embodiments of headgear illustrated in FIGS. 1-4, various alternatives to the system 10 may be embodied in various bands 12 or caps 30 or combinations thereof. As a practical matter, the housings 14 may be embodied in earflaps 16 associated with caps 30 or top portions 30. That is, a band 12 may be part and parcel of, integrated completely and seamlessly within, the top portion 30, to form a cap 30. On the other hand, a cap 30 may be a top portion 30 fastened to a band 12. In any event, whether an isolated band 12, an integrated cap 30 that includes the band integrally and inseparably, even seamlessly, attached, or a band 12 that has been seamed, sewn, bonded, or otherwise attached to a top portion 30, the earflaps 16 are best provided in a configuration that extends down to cover the ears of a user, while leaving the face free for sight, breathing, and so forth.

Thus, in general, the earflaps 16 may form all or part of the housings 14 over the ears, respectively. Likewise, any type of decoration 34 that may be printed on, be attached to, extend from, or otherwise be connected with a cap 30 may be added, included, integrated, or the like. Typically, the decoration 34 is a design choice or an arbitrary aesthetic choice of a user or designer. Typically, decorative elements 34 will not influence the function, design, appearance, configuration, or science of the earmuffs 20 located within the housings 14.

In one embodiment, the earflaps 16 may include straps 32 or ties 32 for securing the earflaps 16 together around the jaw line or chin of a wearer. Meanwhile, straps 36 may include closures such as snaps, hook-and-loop fasteners, buttons, buckles, or the like. Regardless of whether the straps 36 or the ties 32 are relied upon, or entirely absent, the earflaps 16 are best able to function to maintain coverage if a degree of tension in a circumferential direction around the crown of the head, or in a circumferential path under the chin and over the top of the crown of the head, exists in the headgear system 10. The strap 32, 36 or the headband 12 applying a circumferential tensile force is valuable in the operation of the earmuffs 20. For example, the circumferential tension applied to the earflaps 16 supports a snug compressive force against the earmuffs 20, transmitted through the housings 14.

Referring to FIGS. 5-20, while continuing to refer generally to FIGS. 1-23, earmuffs 20 in accordance with the invention may rely on a shell 40 formed of an elastomeric polymer formed to fit around an ear of a user. The material selected for molding, forming, shaping, or otherwise manufacturing a shell 40 should be selected to have a durometer value of hardness (the reciprocal of softness, qualitatively) that is close to that of human tissue.

Specifically, the thickness, material properties, dimensions, bending stress, and so forth may be selected such that the shell 40 itself acts approximately the same in resistance, deformability, mechanical properties, or flexure as the human ear. To the touch, the material of the shell 40 should approximate of skin or human flesh. In this way, pressure exerted against any portion of the head of a wearer is limited by the size, shape, and material properties of the configuration and material of the shell 40. In this way, the comfort may be assured of a user who is often incapable of a specific complaint, may be assured.

In the illustrated embodiments, the shell 40 may be formed to have an outer surface 41 that will receive sound waves impinging thereon from the environment surrounding a wearer. Meanwhile, a flange 42 may be used as a manufacturing device for delivery of resin into a mold, as well as a fastening mechanism for securing the shell 40 into the housing 14.

In the illustrated embodiments, the flange 42 may be included in manufacture only, manufacturing and installation, or may be present in manufacture and removed for assembly. In yet other embodiments, the flange 42 may be completely dispensed with, and the shells 40 may be manufactured by any suitable polymeric molding process. Absent the flange 42, positioning and securing the shells 40 to the housing portion 14 of the earflaps 16 may require bonding, fastening, clipping, pinning, sewing, or other fastening mechanisms in order to stabilize and position the shells 40 to surround the ears of a wearer.

The inner surface 43 of the shell 40 may or may not touch the head or ears of a wearer. In currently contemplated embodiments, the pocket 44 or cavity 44 formed in the interior of the shell 40 by the inner surface 43 of the shell 40 receives an ear of a user. Nevertheless, the pocket 44 may be shaped in one of several ways.

For example, in the illustrated embodiments, the pocket 44 is monotonically decreasing in effective diameter as one proceeds along an axis perpendicular to the flange 42, and from the flange 42 outboard toward the offset wall 46 and outer wall 48. In other embodiments, depending on manufacturing technique, the pocket 44 may expand in effective diameter before closing back to a reduced diameter at the outer wall 48, if at all.

Nevertheless, it has been found that for the ears of infants, the proportions of the shell 40 as illustrated serve adequately. In the illustrated embodiment, the rim 50 is the only portion of the shell 40 in contact with the person of a wearer. For example, the offset wall 46 has an effective diameter encircling an axis passing through the center thereof. It is perpendicular to the flange 42, approximately perpendicular to the outer wall 48, which is adequate to receive an ear of a user, and still accommodate additional padding.

The rim 50 specifically remains completely empty. For example, the rim 50 is designed to form or encompass a continuous, uninterrupted, completely closed loop having a U-shaped cross-section. That shallow U cross-section has an outer leg in contact with a head of a user beside the ear of the user. That leg of the U is free to bend, fold, collapse, or the like, in order to relieve any localized stress.

For example, the shape of a head of a user is not a flat plane. Below and behind the ear, the skull typically recedes away from the ear. Accordingly, the straps 32, 36, securing the earflaps 16 will tend to form the housings 14 around the head of a user. The housing 14 will itself tend to load the shell 40 and bend it to conform to the head of a user. Bending stresses may bend the shell 40, thus bringing the rim 50 into complete contact about its entire circumference against the head of a user. To the extent that localized adjustments are necessary or valuable, they will be automatically made by deflection of the shell 40 itself. Generally, in response to bending loads, or by localized deflection or even collapse of the outer leg of the U cross-section of the rim 50, an effectively air-right seal is made by the rim against the head.

It has been found particularly useful in an embodiment of the shell 40 in accordance with the invention to have the rim 50 of about the same wall thickness as the offset wall 46, the outer wall 48, and so forth. The flange 42 being of the same thickness is less important, but may be of the same thickness in order to assist in manufacturing and assembly (e.g., sewing, stitching, etc.) processes. For example, an injection mold works most efficiently if all web thicknesses being molded are of the same dimension or value. A thin wall is also more easily penetrated for stitching.

The flexible material of the shell 40 may be any suitable material such as polyurethane, neoprene, silicone, or other elastomeric polymers having the proper durometer hardness values, structural strength, ultimate tensile strength, deflection with load, resilience, elasticity, and so forth.

In general, the offset wall 46 serves to offset the outer wall 48 away from both the flange 42 and the rim 50. Thus, the offset wall 46 proceeds from the corner 52 or vertex 52 between the flange 42 and the offset wall 46 extends toward the outer wall 48. Thus, the offset wall 46 begins as a continuous, contiguous, homogeneous material formed with the flange 42. It proceeds from the corner 52 defined by circumferential curve in the illustrations. It proceeds outward, but angled toward its central axis, ultimately arriving at the corner 54 or vertex 54. That vertex 54 is represented by another curve extending circumferentially at a smaller effective radius and circumference.

For purposes of this description, effective diameter is considered to be a hydraulic diameter. A hydraulic diameter is twice a hydraulic radius. A hydraulic radius is four times an area divided by its perimeter. Thus, an effective diameter may be calculated for the outer wall 48 and the inner and outer corners 52, 54 (vertices 52, 54) that bound the offset wall 46, and the rim 50.

Likewise, an effective diameter for the flange 42 may be calculated. Thus, it is proper herein to speak of an effective diameter, since features of the shell 40 need not be, and indeed are not shown to be, exactly circular in any of the illustrated embodiments. Circular embodiments are possible, but raise other manufacturing and fit issues for use by a wearer, given the natural shape of ears.

Figure 21:
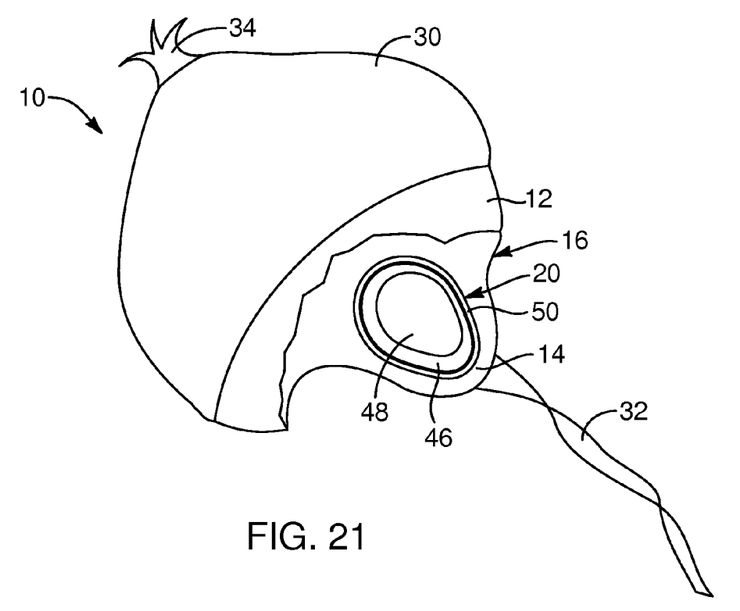
FIG. 21 is a partially cut away perspective view of an alternative embodiment of headgear in accordance with the invention, illustrating the sound-reducing earmuff installed in the housing formed in an earflap of the headgear.
Figure 22:
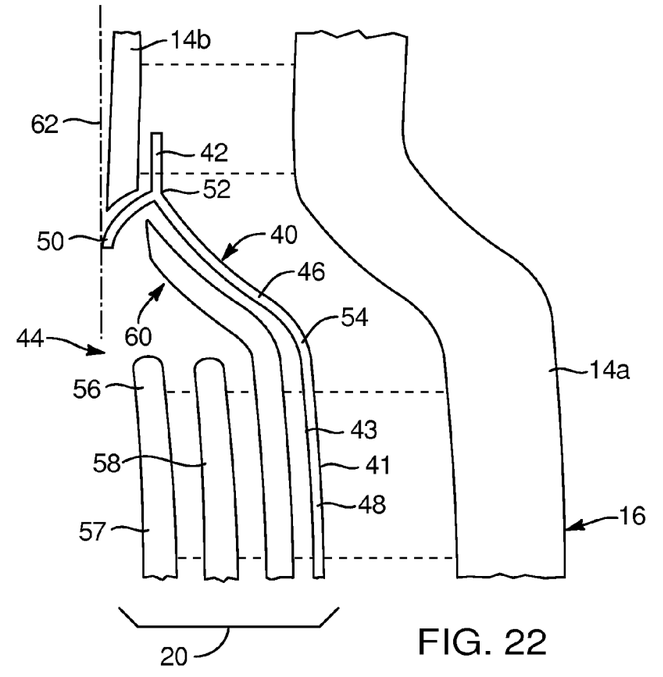
FIG. 22 is a partially cut away, cross-sectional view of the upper portion of the earmuff and housing expanded in exploded view.
Figure 23:
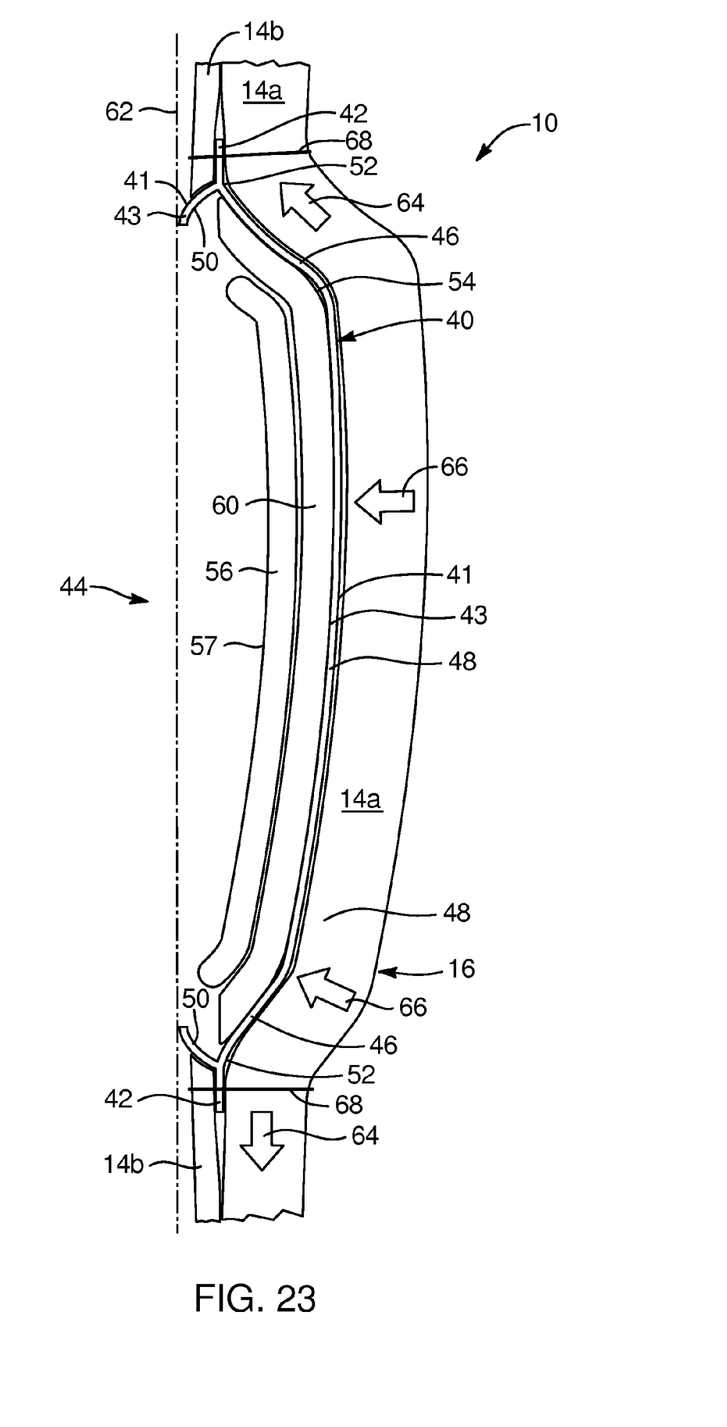
FIG. 23 is a rear elevation, partially cut away, cross-sectional view of a housing and earmuff in accordance with the invention.

Referring to FIGS. 21-23, while continuing to refer generally to FIGS. 1-23, a system 10 or headgear 10 in accordance with the invention may have sewn into or otherwise secured between different layers 14a, 14b of the housing 14 a flange 42 of a shell 40. In the illustrated embodiment, the layers 14a, 14b may be thought of as an outside layer 14a, and an inside layer 14b of a housing 14. The inside layer 14b is not necessarily required.

For example, the flange 42 may be secured directly to the outside layer 14a. Nevertheless, for aesthetics and comfort, as well as warmth, the housing 14 may be made as two portions 14a, 14b. It should also be noted herein that a trailing reference letter signifies a specific instance of an item identified by the reference numeral. Accordingly, it is proper to speak of a housing 14 as well as a housing 14a, 14b, or the like.

Referring to FIG. 22, one embodiment of an apparatus and system 10 in accordance with the invention may provide a stackup beginning at an outermost extreme with a layer 14a of a housing 14. Inside the housing 14a is contained a shell 40 providing an inner surface 41, a flange 42, and an outer surface 43, all defining a pocket 44 or cavity 44 to receive an ear of a user wearing the headgear 10. In the illustrated embodiment, the rim 50 is formed inboard (toward the wearer) of the flange 42. Accordingly, when the inner layer 14b of the housing 14 is positioned inboard of the flange 42, the flange 42 may be sewn, bonded, stitched, tied, stapled, riveted, or otherwise fastened between the two layers 14a, 14b of the housing 14. Thus, the shell 40 may be stabilized within the earflap 16 of the headgear 10.

As illustrated, the inner wall 43 of the shell 40 may receive various additional components. For example, closest to the actual skin of a user may be a contact layer 56. The contact layer 56 may formed of the same material as the housing 14. Typically, a contact layer 56 may be formed of fleece, terry cloth, synthetic fur, or other soft, insulating fabric pleasant to the touch. In cold weather, the contact layer 56 may form part of a comfort system providing not only soft contact, but insulation value against outdoor temperatures. For example, if the shell 40 were exposed to outside temperatures on the outer surface 41, and had no additional lining elements on the inside surface 43, it may not provide the secondary benefit of sufficient warmth for the wearer.

A contact surface 57 may actually contact the skin, typically on the ear. It may possibly touch on a portion of the head, but typically only the ear of a user. Similarly, an optional layer 58 may operate as a filler or deflection layer 58. Typically, the layer 58 is a compliant, virtually unresistant, open-cell elastomeric foam. It is entirely optional. However, sound deadening material, thermally insulating material, comparatively soft (low spring constant) easily deflected material or the like may be used in an optional layer 58.

Meanwhile, a liner 60 is typically is installed along the entire interior surface 43 of the shell 40, outboard of the rim 50. Inelastic, sound dampening, memory foam serves well.

For example, the rim 50 is typically completely empty in order to accommodate its need for deflection and deformability to fit against the head of a wearer.

By contrast, the liner 60 typically is formed of an expanded elastomeric polymer. Thus, urethane, neoprene, or the like containing embedded air bubbles may be formed as an open-cell or closed-cell foam. Typically, a closed-cell foam will tend to deaden the sound. However inelastic foams (e.g., memory foam) may be open-cell types. The liner 60, when formed of inelastic material tends to dampen sound by delaying transmission because it is deformable inelastically. Various types of foam, such as memory foam, and other theologically inelastic materials may actually return elastically to their initial position, but with such a delay that sound, deflection, force, and the like are not immediately transmitted as would be the case in exactly elastic material.

The liner 60 may be bonded to the inside surface 43 of the shell 40. The liner 60 may extend along the inside surface, entire outer wall 48, and even along all or part of the offset wall 46 provides the offset by spacing the outer wall 48 away from the rim 50.

In general, the surface of the head of a user may present a contact line 62 or contact plane 62. The contact line 62 may be outboard from the rim 50. The first compliance or deflection in order to accommodate movement by a user of the contact line 62 in an outboard direction is the rim 50. The rim 50 may deflect to accommodate any variation from an absolute planar configuration along the contact line 62. Put another way, the rim thereof may be bendable in response to pressure exerted thereagainst from a surface of the skin of the wearer.

For example, the entire outer most edge of the rim 50 may typically be in contact with a plane 62. Nevertheless, the head of a user is not a plane. It is not planar and may necessarily deflect portions of the rim 50 about its circumference as necessary. The rim 50 provides a comparatively minimal deflection defined by the thickness of the rim 50 or the wall of the rim 50 and the distance from the flange 42 out to the contact line 62 or contact plane 62.

The bending deflecting of the shell 40 may be greater than that of the rim 50. Beam deflection of the rim may occur with a degree of resistance, inasmuch as the entire circumference of the rim 50 is uninterrupted. Nevertheless, the rim 50 may roll under itself or collapse locally in order to accommodate deflections, with only nominal force required. Thus, the rim 50 is able to maintain a substantially airtight seal against the head, around the ear of a user.

Meanwhile, if the rim 50 deflects sufficiently, the contact plane 62 or contact line 62 will next be met by the housing layer 14b. The layer 14b may typically be formed of a loose fabric such as a fleece, felt, knit, or other comparatively soft and deformable material. Thus, the head of a user may contact the layer 14b when the contact line 62 is deflected sufficiently to the right in the illustrated embodiment.

Additional deflection may also be available to a user in reliance on the outer layer 14b of the housing 14. For example, the arrows illustrate tension forces 64 existing within the outer layer 14b of the housing 14 due to the ties 32, 36 securing the earflaps 16 toward one another. In an embodiment that relies only on a flexible circumferential band 12, the direction of the forces 64 will be different. Nevertheless, a tensile force acting circumferentially about the crown of the head may be applied.

The resultant force vector acting on the shell 40 as a result of the tensile forces 64 in the housing portion 14a may be compressive in nature. Thus, the arrows 66 showing compressive forces 66 tend to provide deflection, such as by beam bending, in the cross section of the shell 40. By so doing, the outer layer 14a may apply sufficient loading to deform or deflect the shell 40 in beam bending. Thus, in addition to the deflection of the rim 50, the entire shell 40 may deflect, rendering it more easily conformal to the shape of the head of a wearer.

The dimensions of thickness, length, width, circumference, and so forth are selected, and particularly the wall thickness, in order to provide an ease of deflection that corresponds to about the same levels of force and stress as would deflect skin or bend an ear of a user. Thus, when in contact with the ear of a user, the system 10 and the skin and ear of a user may provide about the same levels of force against one another. In this way, the system 10 provides deflection to accommodate the shape of the head of ears of a user, without causing undue stress, and consequent development of pain.

It has been found that pressure on tissue tends to restrict circulation of blood within tissue. A lack of circulation causes pain after a period of minutes. Pressure often causes development of sores and necrosis over a period of days. In the use of headwear 10, it is unlikely that a user or wearer would wear the headgear for days at a time uninterrupted. Nevertheless, the headgear may be worn for minutes or hours within a day, thus making pain a significant element to be avoided.

Stitches 68 or stitching 68 may pass from the outside of each of the layers 14a, 14b of the housing 14 through to one another, by way of the flange 42. In the alternative embodiments lacking a flange 42, the shell 40 may be bonded to one or more of the layers 14a, 14b. Glue, heat, melting of base material in the housing 14, shell 40, or both, riveting, stapling, or the like may still be done to secure the outer wall 48, for example, to the outer layer 14a.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. A method for protecting hearing of an infant, the method comprising:
   providing headgear containing an earmuff, the earmuff being formed to have a she portion, a liner portion contained completely within the shell portion, a housing portion covering the shell portion, and a contact layer inside the shell portion, wherein the she portion is formed of an elastomeric polymer material sized and shaped to deflect in bending in response to compressive forces imposed by the housing and wherein the contact layer is configured to make physical contact with an ear of a wearer;

placing the earmuff over the ear of the wearer by placing the headgear on the head of the wearer;

securing the earmuff against the head of the wearer by the compressive forces exerted by the housing toward the wearer; and conforming the she to the shape of the head of the wearer in response to the compressive forces exerted by the housing.

2. The method of claim 1, wherein the contact layer is formed of a material configured to and selected to deflect in response to pressure exerted by the ear of the wearer.

3. The method of claim 1, further comprising deflecting by a rim of the housing in response to tensioning of the housing.

4. The method of claim 1, further comprising forming, by a rim of the housing, a sound-resistant seal between the rim and the head of the wearer.

5. The method of claim 1, comprising blocking, by the shell, sound propagated from the environment surrounding the wearer against impingement upon the eardrum of a user.

6. The method of claim 1, wherein the shell comprises an outer wall, an offset wall, a rim, and a flange, all formed continuously, contiguously, and homogeneously of a single material.

7. The method of claim 6, wherein the single material of the shell is selected to have a deflection within the shell selected to conform to the head of the wearer comfortably.

8. The method of claim 6, wherein the material of the shell is selected to be impervious to passage of fluid therethrough, and the offset wall and the outer wall are formed to have approximately a single constant wall thickness, the rim thereof configured to bend in response to pressure exerted thereagainst from a surface of the skin of the wearer.

* * * * *

UNITED STATES PATENT AND TRADEMARK OFFICE
CERTIFICATE OF CORRECTION

PATENT NO. : 9,585,792 B2
APPLICATION NO. : 13/725226
DATED : March 7, 2017
INVENTOR(S) : Jacob Frederick Fairclough et al.

Page 1 of 1

It is certified that error appears in the above-identified patent and that said Letters Patent is hereby corrected as shown below:

In Claim 1, Line 4 (found at Column 10, Line 65) "she" should be shell.

In Claim 1, Line 7 (found at Column 11, Line 1) "she" should be shell.

In Claim 1, Line 18 (found at Column 11, Line 12) "she" should be shell.

Signed and Sealed this
Twenty-first Day of November, 2017

Joseph Matal
*Performing the Functions and Duties of the
Under Secretary of Commerce for Intellectual Property and
Director of the United States Patent and Trademark Office*